(12) United States Patent
Chang et al.

(10) Patent No.: US 11,417,310 B2
(45) Date of Patent: Aug. 16, 2022

(54) INSPECTION DEVICE

(71) Applicant: Quanta Computer Inc., Taoyuan (TW)

(72) Inventors: Chia-Yuan Chang, Taoyuan (TW);
Jung-Wen Chang, Taoyuan (TW);
Kao-Yu Hsu, Taoyuan (TW);
Tung-Han Lee, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 171 days.

(21) Appl. No.: 17/068,044

(22) Filed: Oct. 12, 2020

(65) Prior Publication Data
US 2021/0358472 A1    Nov. 18, 2021

(30) Foreign Application Priority Data

May 13, 2020 (TW) ................................. 109205785

(51) Int. Cl.
*G10K 11/34*     (2006.01)
*A61B 7/04*      (2006.01)

(52) U.S. Cl.
CPC .............. *G10K 11/341* (2013.01); *A61B 7/04* (2013.01)

(58) Field of Classification Search
CPC .................................. G10K 11/341; A61B 7/04
See application file for complete search history.

(56) References Cited

U.S. PATENT DOCUMENTS

| | | | | |
|---|---|---|---|---|
| 2015/0297171 | A1* | 10/2015 | Thiagarajan | A61B 5/0205 381/300 |
| 2016/0100817 | A1* | 4/2016 | Hussain | A61B 7/04 600/528 |
| 2020/0205770 | A1* | 7/2020 | Friedman | H04R 1/1025 |
| 2021/0169417 | A1* | 6/2021 | Burton | A61B 5/4857 |
| 2021/0345939 | A1* | 11/2021 | Jumbe | H04R 1/46 |
| 2021/0378625 | A1* | 12/2021 | Lin | A61B 7/02 |

FOREIGN PATENT DOCUMENTS

| | | | | |
|---|---|---|---|---|
| CN | 104023624 A | * | 9/2014 | ............ A61B 5/002 |
| CN | 215227799 U | * | 12/2021 | |
| WO | WO-2022040353 A2 | * | 2/2022 | |

* cited by examiner

*Primary Examiner* — David L Ton
(74) *Attorney, Agent, or Firm* — McClure, Qualey & Rodack, LLP

(57) ABSTRACT

An inspection device is provided, including a base, a circuit assembly, an electrocardiogram sensor, a diaphragm, an annular member, and a positioning member. The base has a top surface, a bottom surface, a guiding portion, an opening, and an accommodating space. The guiding portion is formed on the top surface, the opening is formed on the bottom surface, and the accommodating space is formed between the top surface and the bottom surface. The circuit assembly is disposed in the accommodating space, and has a first contact and a second contact. The electrocardiogram sensor is disposed on the bottom surface and electrically connected to the circuit assembly. The diaphragm covers the opening. The annular member is rotatably connected to the base and has a guiding member. The guiding member is slidably connected to the guiding portion. The positioning member is affixed to the annular member and has a contacting portion.

10 Claims, 11 Drawing Sheets

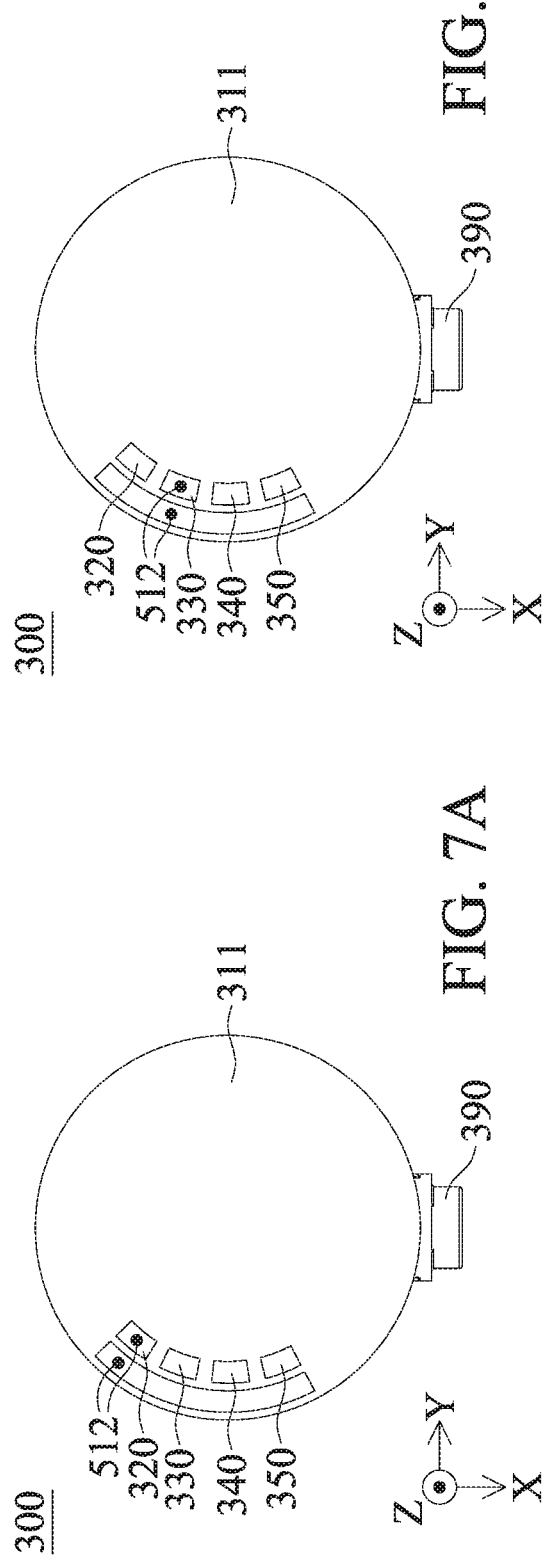
FIG. 7A
FIG. 7B
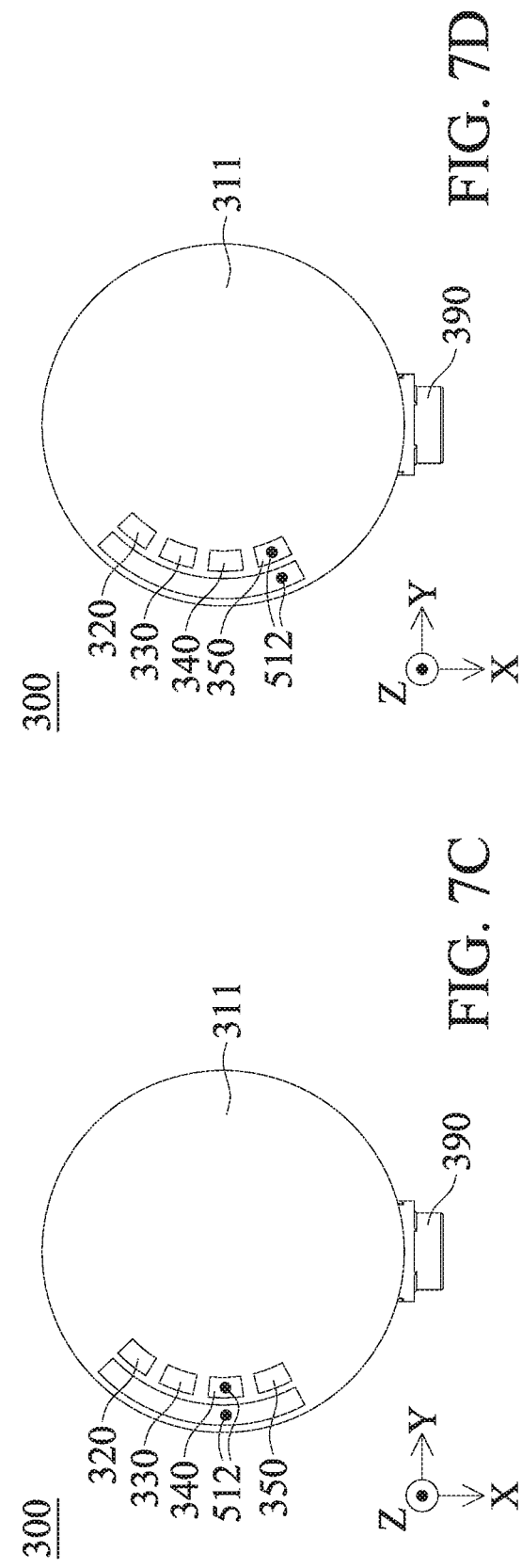
FIG. 7C
FIG. 7D

INSPECTION DEVICE

CROSS REFERENCE TO RELATED APPLICATIONS

This application claims the benefit of Taiwan Patent Application No. 109205785, filed May 13, 2020, the entirety of which is incorporated by reference herein.

BACKGROUND OF THE INVENTION

Field of the Invention

The application relates in general to an inspection device, and in particular, to an inspection device for listening to cardiopulmonary sound and measuring electrocardiography.

Description of the Related Art

There are a lot of measuring methods to obtain the health condition of the human body. For example, using a stethoscope to listen to the sounds inside the human body (such as the heart beat) is one common diagnosis method. However, a conventional stethoscope can merely directly listen via the chestpiece while in use, and cannot simultaneously record the sound when diagnosing. Moreover, the stethoscope cannot simultaneously record other physiological data of the human body when diagnosing. The user has to spend more time and use different apparatuses to measure other physiological data, which can be inconvenient for the user. Therefore, how to address the aforementioned problem has become an important issue.

BRIEF SUMMARY OF INVENTION

An embodiment of the invention provides an inspection device, including a base, a circuit assembly, an electrocardiogram sensor, a diaphragm, an annular member, and a positioning member. The base has a top surface, a bottom surface, a guiding portion, an opening, and an accommodating space. The guiding portion is formed on the top surface, the opening is formed on the bottom surface, and the accommodating space is formed between the top surface and the bottom surface. The circuit assembly is disposed in the accommodating space, and has a first contact and a second contact. The electrocardiogram sensor is disposed on the bottom surface and electrically connected to the circuit assembly. The diaphragm covers the opening. The annular member is rotatably connected to the base and has a guiding member. The guiding member is slidably connected to the guiding portion. The positioning member is affixed to the annular member and has a contacting portion. When the annular member is in a first position relative to the base, the contacting portion is in contact with the first contact. When the annular member is in a second position relative to the base, the contacting portion is in contact with the second contact.

In some embodiments, the guiding portion is an arc-shaped slot, and the guiding member is a pillar.

In some embodiments, the positioning member is flexible, and has a first recess and a second recess. The inspection device further comprises an engaging member affixed to the base. When the annular member is in the first position relative to the base, the engaging member is joined to the first recess. When the annular member is in the second position relative to the base, the engaging member is joined to the second recess. In some embodiments, the engaging member is a ball.

In some embodiments, the inspection device further comprises a pressing assembly and a trigger assembly. The pressing assembly is flexible and has a pressing member. The trigger assembly has a switch. When an external force is applied to the pressing member, the pressing member deforms and makes contact with the trigger assembly. In some embodiments, the pressing member has a display function, and is electrically connected to the circuit assembly.

In some embodiments, the base has a through hole, and the circuit assembly comprises a headset socket, wherein the through hole communicates the accommodating space with an external environment, and a through hole of the headset socket is aligned with the through hole.

In some embodiments, the inspection device further comprises a temperature sensor disposed on the bottom surface, and the temperature sensor is electrically connected to the circuit assembly. The electrocardiogram sensor comprises two electrodes, and the temperature sensor is disposed between the electrodes.

In some embodiments, the circuit assembly further comprises a wireless transmitting unit. The distance between the circuit assembly and the diaphragm is greater than the distance between the circuit assembly and the annular member. The appearance of the inspection device has a chestpiece structure of the stethoscope.

BRIEF DESCRIPTION OF DRAWINGS

Aspects of the present disclosure are best understood from the following detailed description when read with the accompanying figures. It should be noted that, in accordance with the standard practice in the industry, various features are not drawn to scale. In fact, the dimensions of the various features may be arbitrarily increased or reduced for clarity of discussion.

FIG. 7A is a schematic diagram of a contacting portion and the circuit assembly when an annular member is in a first position relative to a base according to an embodiment of the invention;

FIG. 7B is a schematic diagram of the contacting portion and the circuit assembly when the annular member is in a second position relative to the base according to an embodiment of the invention;

FIG. 7C is a schematic diagram of the contacting portion and the circuit assembly when the annular member is in a third position relative to the base according to an embodiment of the invention;

FIG. 7D is a schematic diagram of the contacting portion and the circuit assembly when the annular member is in a fourth position relative to the base according to an embodiment of the invention;

DETAILED DESCRIPTION OF INVENTION

The making and using of the embodiments of the inspection device are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Unless defined otherwise, all technical and scientific terms used herein have the same meaning as commonly understood by one of ordinary skill in the art to which this invention belongs. It should be appreciated that each term, which is defined in a commonly used dictionary, should be interpreted as having a meaning conforming to the relative skills and the background or the context of the present disclosure, and should not be interpreted in an idealized or overly formal manner unless defined otherwise.

Figure 1:
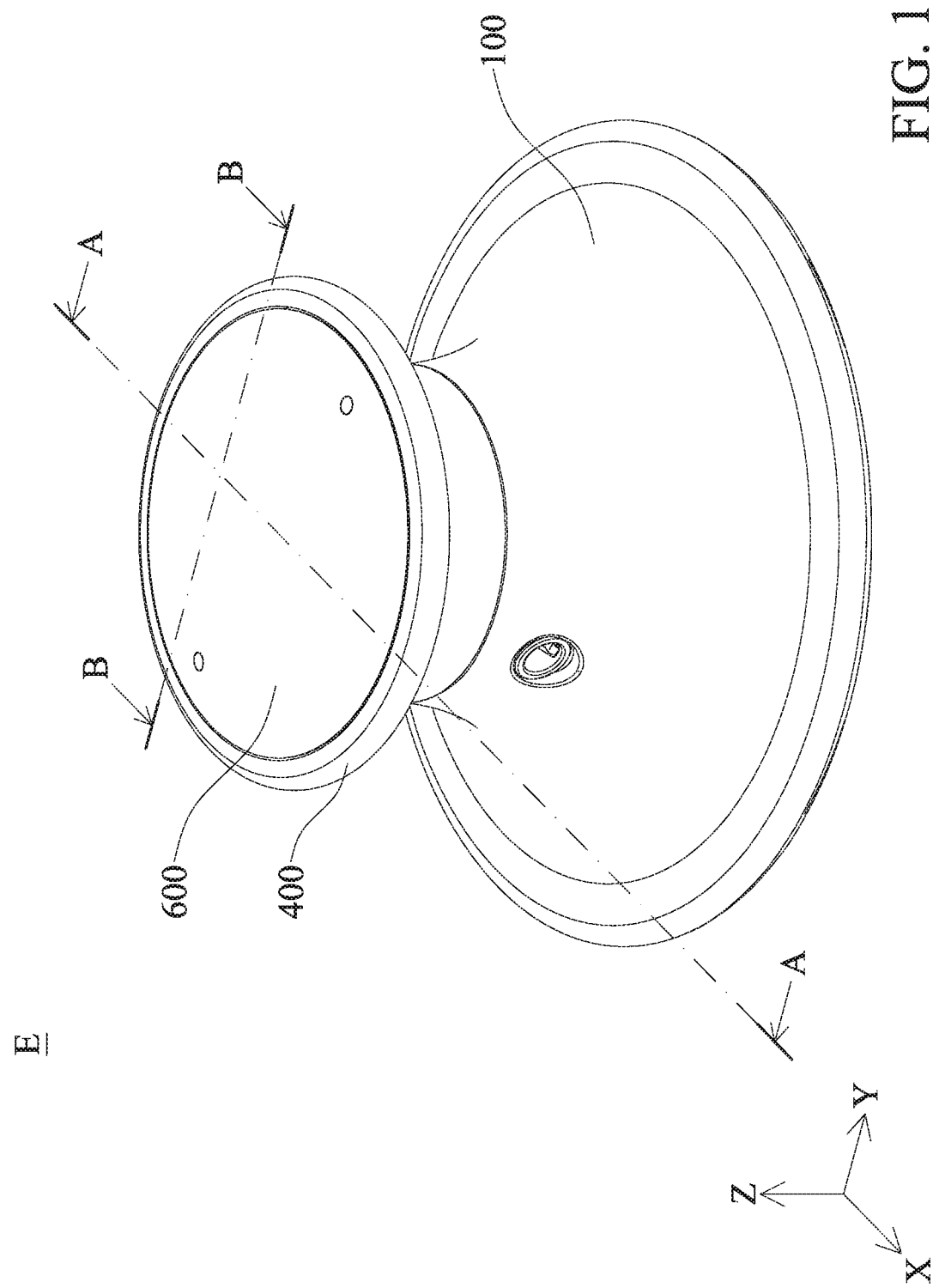
FIG. 1 is a schematic diagram of an inspection device according to an embodiment of the invention.

FIG. 1 is a schematic diagram of an inspection device E according to an embodiment of the invention. The appearance of the inspection device E is formed as a chestpiece structure of a stethoscope. The inspection device E includes a plurality of different functions. For example, the inspection device E can measure and record the electrocardiogram and/or temperature of the human body. In another operation mode, the inspection device E can record the sound inside the human body (such as the heart beat).

Figure 2:
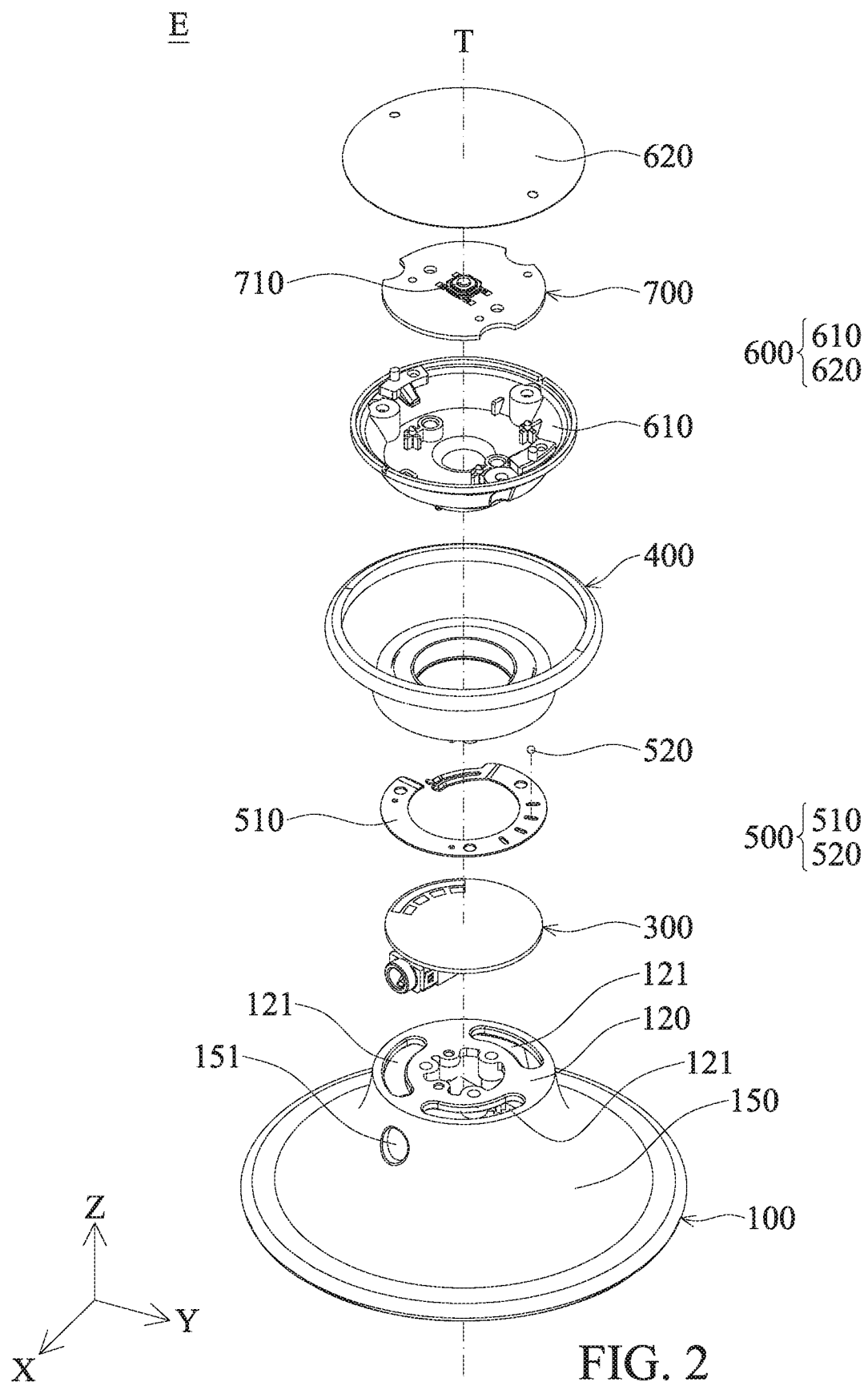
FIG. 2 is a exploded-view diagram of the inspection device according to an embodiment of the invention.
Figure 3:
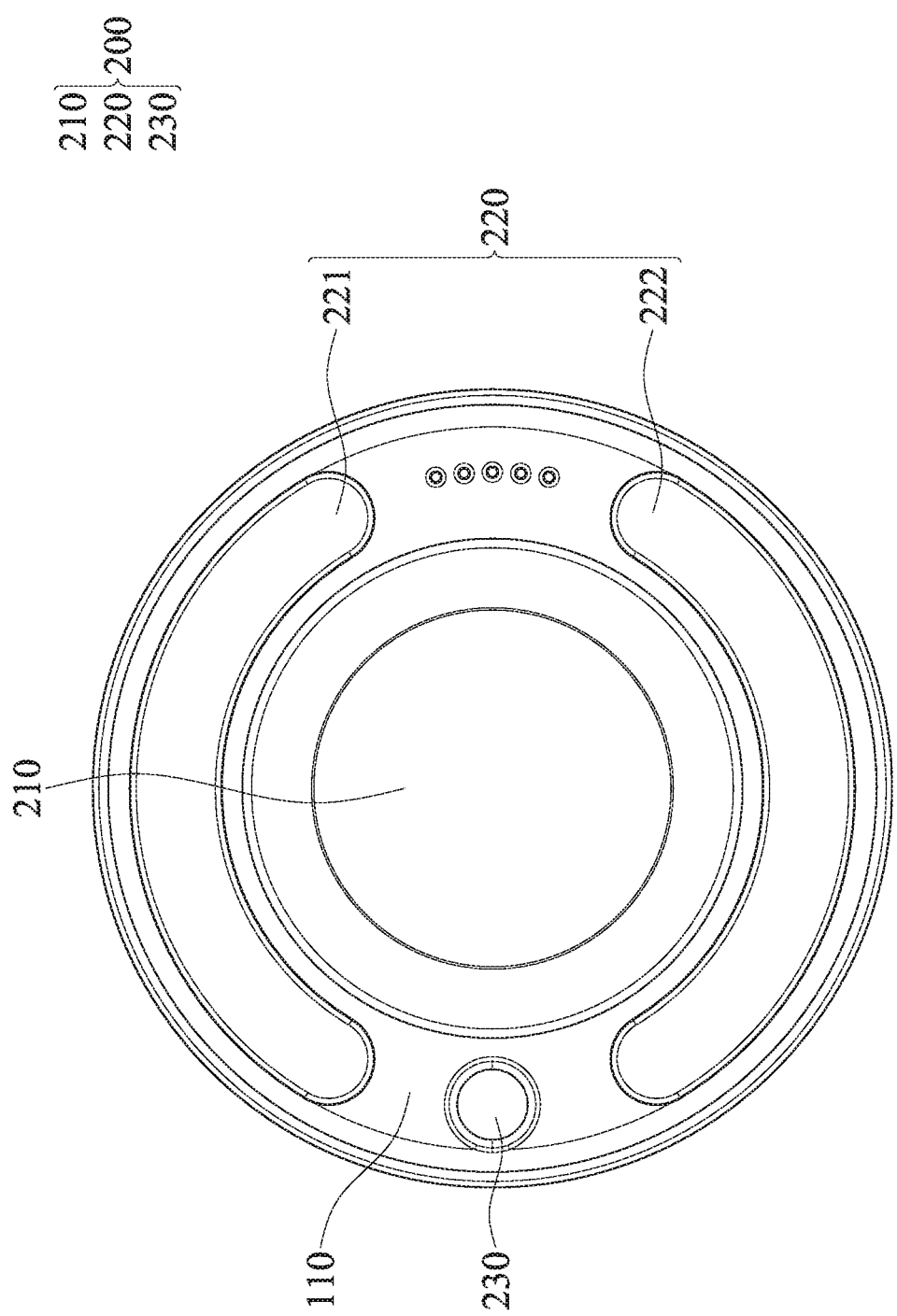
FIG. 3 is a bottom view diagram of the inspection device according to an embodiment of the invention.
Figure 4:
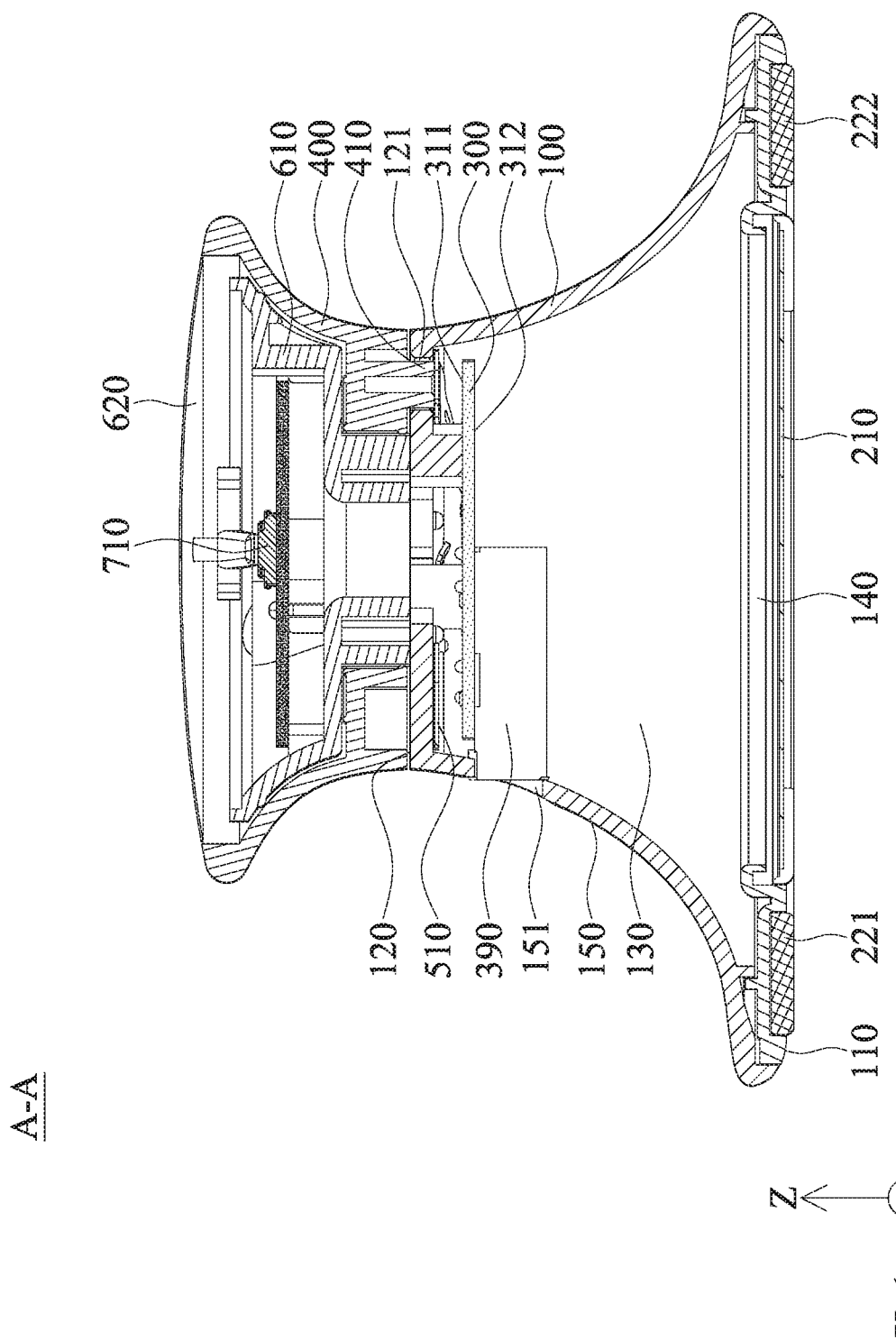
FIG. 4 is a cross-sectional view taken along line A-A of FIG. 1.
Figure 5A:
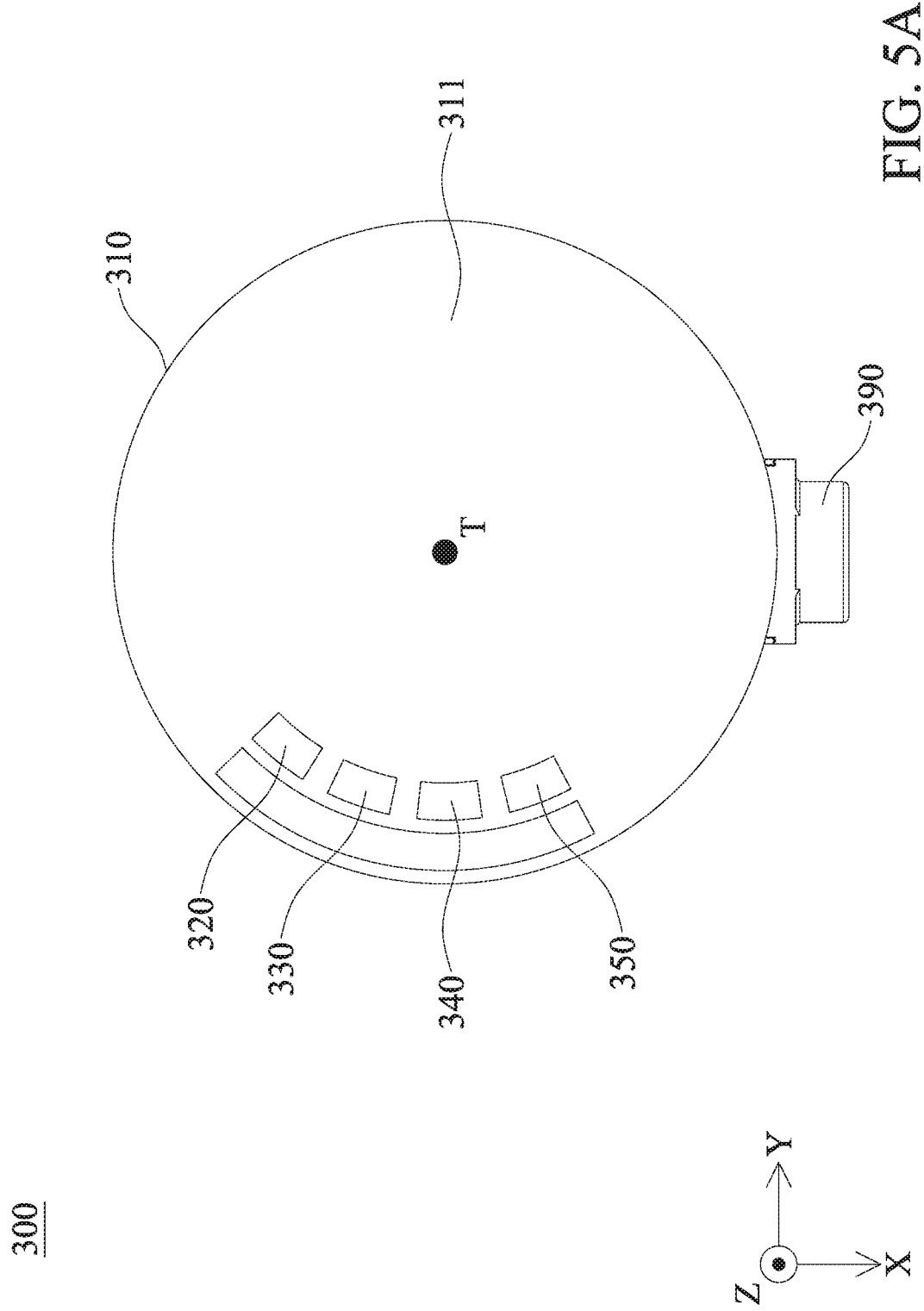
FIG. 5A is a top view diagram of a circuit assembly according to an embodiment of the invention.
Figure 5B:
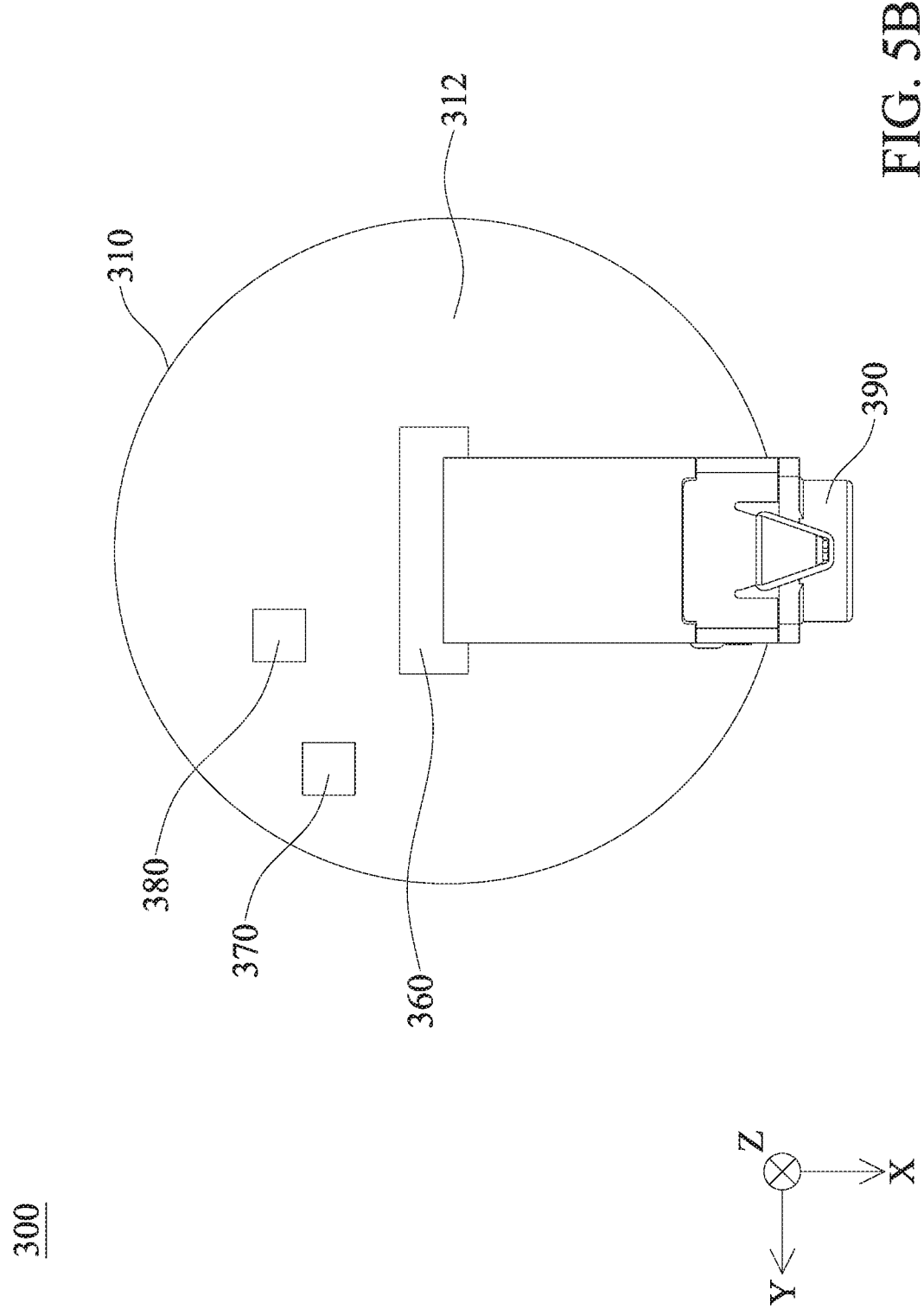
FIG. 5B is a bottom view diagram of a circuit assembly according to an embodiment of the invention.

FIG. 2 is an exploded-view diagram of the inspection device E, FIG. 3 is a bottom view diagram of the inspection device E, and FIG. 4 is a cross-sectional view taken along line A-A of FIG. 1. As shown in FIGS. 2-4, the inspection device E primarily includes a base 100, a sensing module 200, a circuit assembly 300, an annular member 400, a positioning module 500, a pressing assembly 600, and a trigger assembly 700.

The base 100 has a bottom surface 110 and a top surface 120. The bottom surface 110 and the top surface 120 are disposed on the opposite sides of the base 100, and the top surface 120 faces the annular member 400. In order to make the inspection device E to form the chestpiece structure of the stethoscope, the cross-sectional area of the bottom surface 110 of the base 100 is greater than that of the top surface 120. Furthermore, as shown in FIG. 4, an accommodating space 130 is formed between the bottom surface 110 and the top surface 120. The bottom surface 110 has an opening 140, which is communicated with the accommodating space 130. At least one guiding portion 121 is formed on the top surface 120.

As shown in FIGS. 3 and 4, the sensing module 200 includes a diaphragm 210, an electrocardiogram sensor 220, and a temperature sensor 230. The diaphragm 210 is disposed on the bottom surface 110 of the base 100, and covers the opening 140 of the bottom surface 110. Therefore, when the user attaches the bottom surface 110 of the base 100 to the human body, the diaphragm 210 can vibrate due to the acoustic wave, and the accommodating space 130 can be formed as a resonant cavity. The electrocardiogram sensor 220 and the temperature sensor 230 can be also disposed on the bottom surface 110 of the base 100, wherein the electrocardiogram sensor 220 includes two electrodes 221 and 222 surrounding the diaphragm 210, and the temperature sensor 230 is disposed between the electrodes 221 and 222.

Referring to FIGS. 2-4, 5A and 5B, the circuit assembly 300 is disposed in the accommodating space 130 of the base 100. The circuit assembly 300 includes a circuit board 310, at least one first contact 320, at least one second contact 330, at least one third contact 340, at least one fourth contact 350, a sound recording member 360, a storage unit 370, a wireless transmitting unit 380, and a headset socket 390. The circuit board 310 has a first surface 311 and a second surface 312, respectively faces the annular member 400 and the diaphragm 210. The first contact 320, the second contact 330, the third contact 340 and the fourth contact 350 are disposed on the first surface 311, and the sound recording member 360, the storage unit 370 and the wireless transmitting unit 380 are disposed on the second surface 312.

The storage unit 370 is electrically connected to the electrocardiogram sensor 220 and the temperature sensor 230 of the sensing module 200, and further electrically connected to the sound recording member 360 and the storage unit 370. In order to make the resonant cavity of the inspection device E to include a sufficient space, in this embodiment, the distance between the circuit assembly 300 and the diaphragm 210 is greater than the distance between the circuit assembly 300 and the annular member 400. The sound recording member 360 can transform the sound data received from the resonant cavity from the analog signal to the digital signal, and transmit to the storage unit 370 to store. Since the sound recording member 360 is disposed on the second surface 312 facing the diaphragm 210, the sound data is not blocked by the circuit board 310. In this embodiment, the storage unit 370 can be a read only memory (ROM), a flash memory, a random access memory (RAM), or a hard disk drive (HDD).

As shown in FIGS. 2-4 and 5A, the first contact 320, the second contact 330, the third contact 340, and the fourth contact 350, which are disposed on the first surface 311, are arranged along an arc path. The central axis T of the inspection device E passes through the center of the arc path. A through hole 151 is formed on the lateral surface 150 of the base 100, and the through hole 151 communicates the accommodating space 130 with the external environment. The insert hole of the headset socket 390 is aligned with the through hole 151, and the headset socket 390 is electrically connected to the sound recording member 360 or the storage unit 370. When the user desires to use the inspection device E as the chestpiece of a stethoscope, he can insert an external headset into the headset socket 390, and the sound recording member 360 or the storage unit 370 can transmit the sound data to the external headset. Therefore, the user can immediately and directly listen to the sound inside the human body.

Referring to FIGS. 2-4, the annular member 400 is pivotally connected to the base 100, and the chestpiece structure of a stethoscope is formed by the annular member 400 and the base 100. In particular, the annular member 400 has at least one guiding member 410. Since the guiding member 410 is slidably connected to the guiding portion 121 of the base 100, the annular member 400 can rotate around the central axis T relative to the base 100. In this embodiment, the guiding portion 121 is an arc-shaped slot, and the guiding member 410 is a pillar accommodated in the arc-shaped slot. In some embodiments, the guiding member 410 can be an arc-shaped slot, and the guiding portion 121 can be a pillar slidably disposed in the arc-shaped slot.

Figure 6:
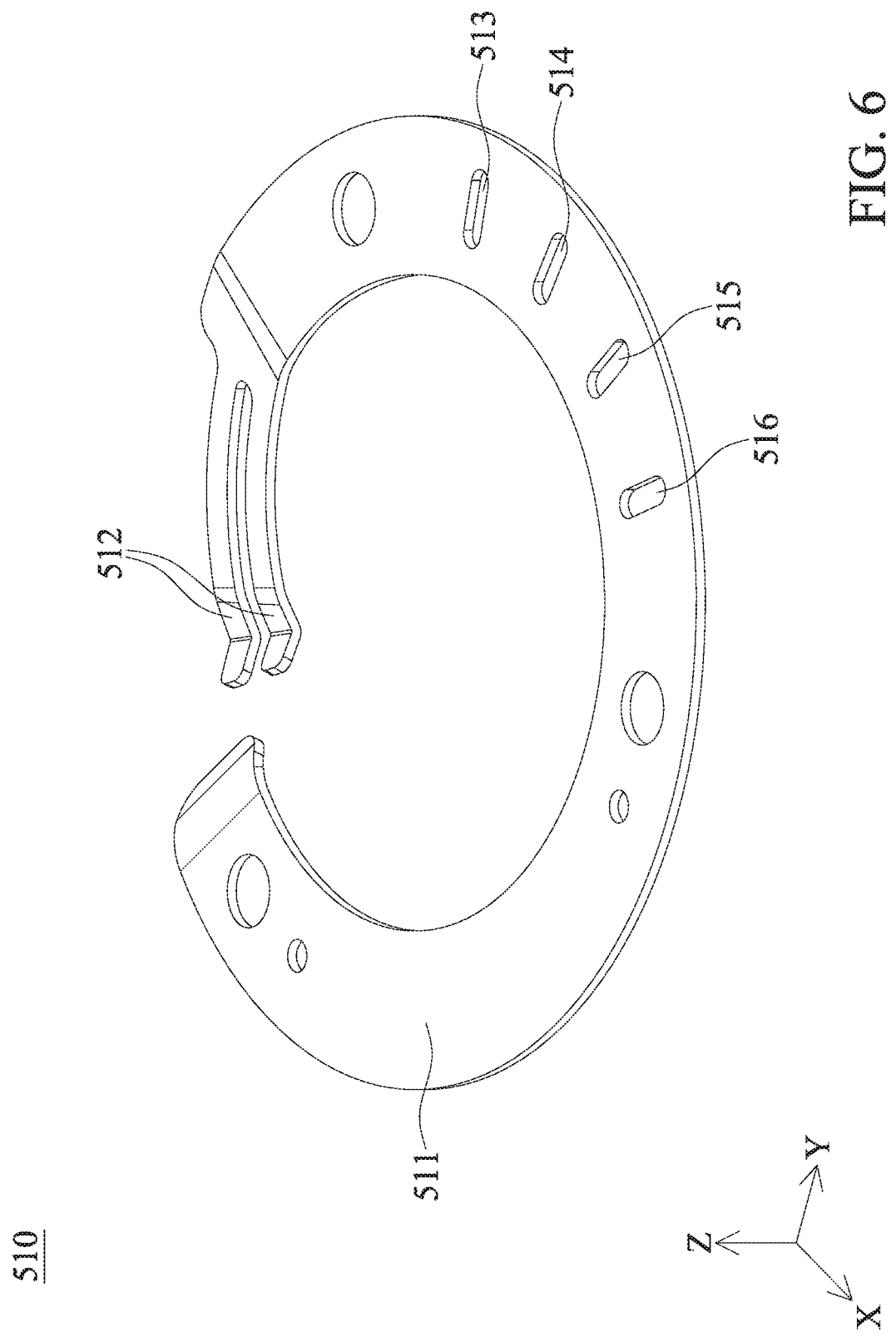
FIG. 6 is a schematic diagram of a positioning member according to an embodiment of the invention.

Referring to FIG. 6, the positioning module 500 includes a positioning member 510, and the positioning member 510 includes a main body 511 and at least one contacting portion 512. In this embodiment, the main body 511 is a sheet spring having an arc-shaped structure, and is flexible. The contacting portion 512 is connected to the main body 511, and extended toward the circuit assembly 300. As shown in FIGS. 2-4, the positioning member 510 is accommodated in the accommodating space 130 and affixed to the annular member 400. Thus, when the annular member 400 rotates relative to the base 100, the positioning member 510 rotates accordingly. The contacting portion 512 of the positioning member 510 can contact the first contact 320, the second contact 330, the third contact 340, or the fourth contact 350 to set the inspection device E in different measure modes.

In detail, as shown in FIG. 7A, when the annular member 400 is in a first position relative to the base 100, the contacting portion 512 is in contact with the first contact 320. At this time, the circuit assembly 300 can transmit signals to the electrocardiogram sensor 220 and the temperature sensor 230. After the electrocardiogram sensor 220 and the temperature sensor 230 receive the signals, they can be enabled and transmit the measured data to the storage unit 370. As shown in FIG. 7B, when the annular member 400 rotates relative to the base 100 to a second position, the contacting portion 512 is in contact with the second contact 330. At this time, the sound recording member 360 can be enabled and receive the sound data. As shown in FIG. 7C, when the annular member 400 rotates relative to the base 100 to a third position, the contacting portion 512 is in contact with the third contact 340. At this time, the electrocardiogram sensor, the temperature sensor 230 and sound recording member 360 can be enabled simultaneously. As shown in FIG. 7D, when the annular member 400 rotates relative to the base 100 to a fourth position, the contacting portion 512 is in contact with the fourth contact 350, and the inspection device is in a closed state.

Figure 8:
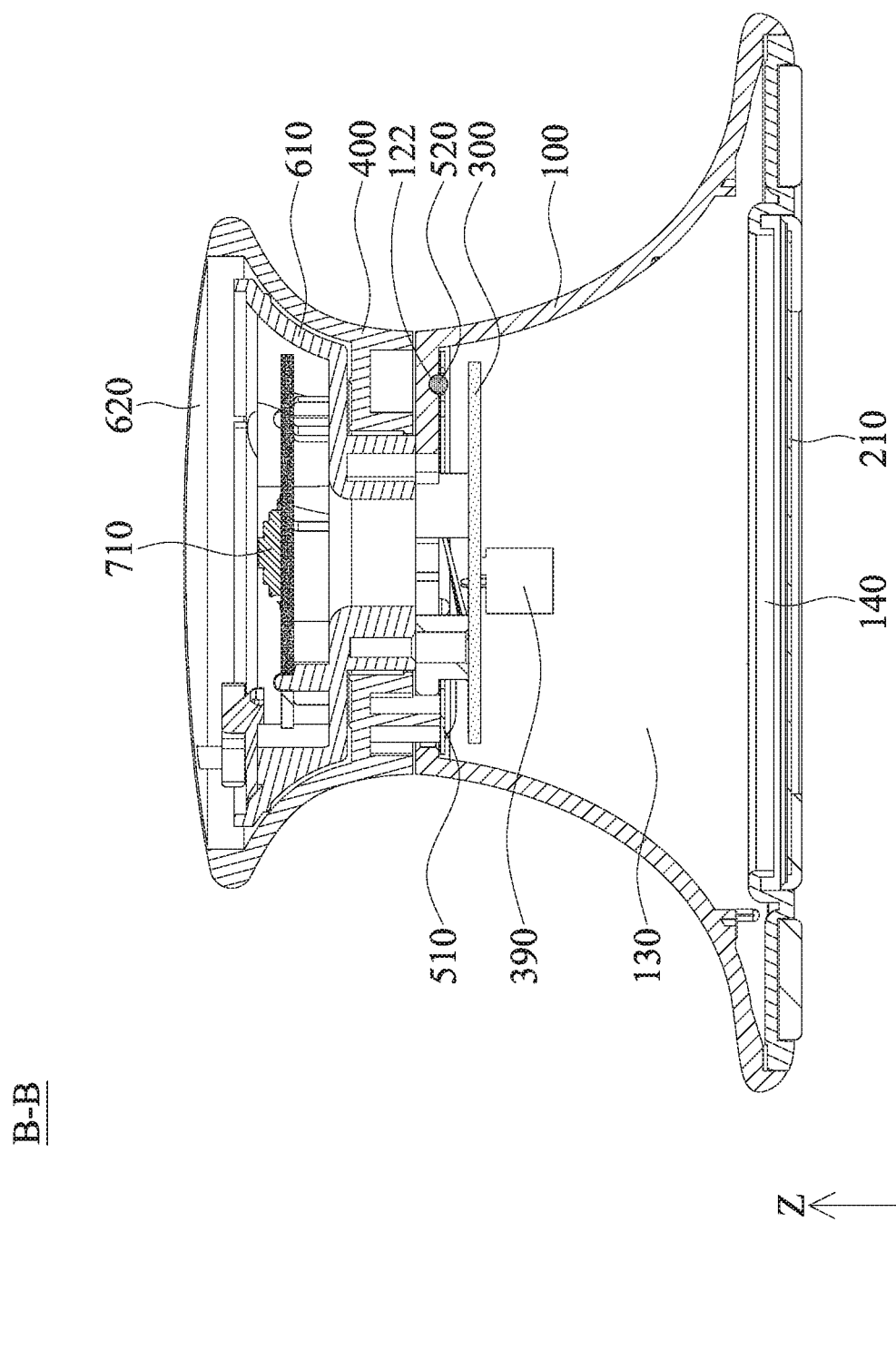
FIG. 8 is a cross-sectional view taken along line B-B of FIG. 1.

Referring to FIGS. 2, 6 and 8, besides the positioning member 510, the positioning module 500 further includes an engaging member 520, and the annular member 400 can be positioned in the first position, the second position, the third position, and the fourth position through the positioning module 500. In this embodiment, the engaging member 520 is a ball, and a first recess 513, a second recess 514, a third recess 515, and a fourth recess 516 are formed on the main body 511 of the positioning member 510.

As shown in FIG. 8, the engaging member 520 is disposed on the base 100, and the position of the engaging member 520 is affixed relative to the base 100. In this embodiment, a depression 122 is formed on the top wall of the base 100, and at least a portion of the engaging member 520 is accommodated in the depression 122, and a portion of the engaging member 520 protruding from the depression 122 is in contact with the positioning member 510.

Figures 9A, 9B, 9C, 9D:
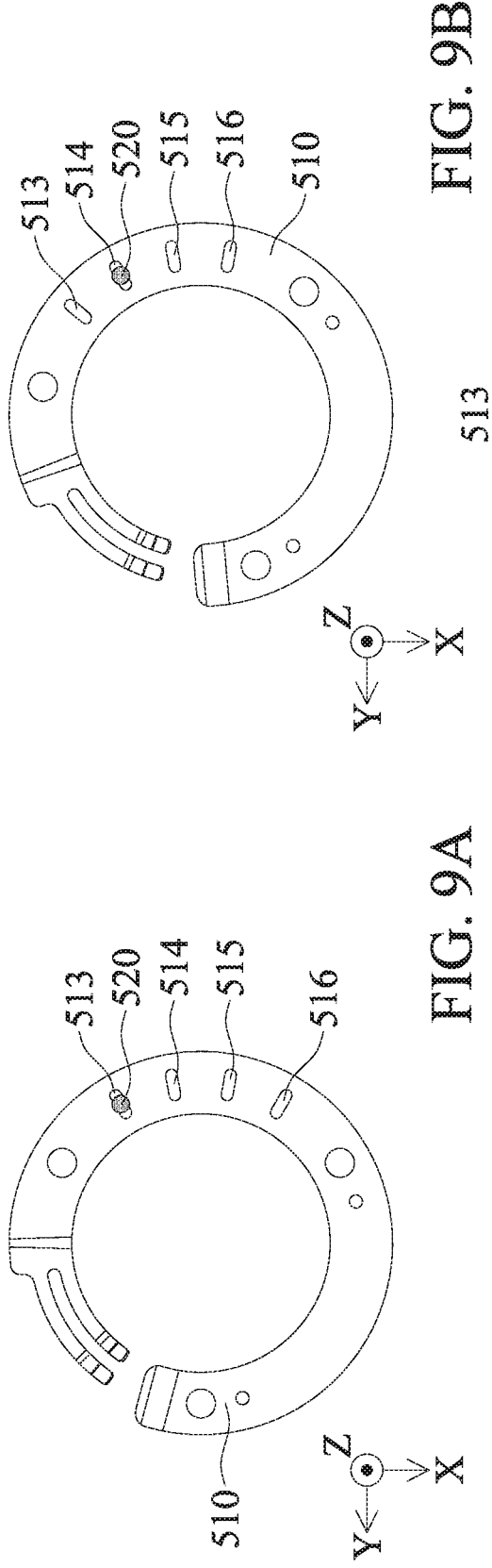
FIG. 9A is a schematic diagram of a positioning member and an engaging member when the annular member is in the first position relative to the base according to an embodiment of the invention.
FIG. 9B is a schematic diagram of the positioning member and the engaging member when the annular member is in the second position relative to the base according to an embodiment of the invention.
FIG. 9C is a schematic diagram of the positioning member and the engaging member when the annular member is in the third position relative to the base according to an embodiment of the invention.
FIG. 9D is a schematic diagram of the positioning member and the engaging member when the annular member is in the fourth position relative to the base according to an embodiment of the invention.

As shown in FIG. 9A, when the annular member 400 is in the first position relative to the base 100, the engaging member 520 enters the first recess 513, so that the annular member 400 can be affixed to the first position. When the user desires to change the operation mode, he can provide the force on the annular member 400 to rotate the annular member 400 relative to the base 100. Since the positioning member 510 is the flexible arc-shaped sheet spring, it can be deformed when the user provides the force. The engaging member 520 can therefore leave the first recess 513 and move on the surface of the positioning member 510, and then enters the second recess 514 adjacent to the first recess 513 (FIG. 9B).

As shown in FIGS. 9B-9D, when the annular member 400 is in the second position, the third position, and the fourth position relative to the base 100, the engaging member 520 respectively enters the second recess 514, the third recess 515, and the fourth recess 516 to affix the annular member 400.

Since the positioning member 510 and the engaging member 520 in this embodiment are made of metal, the debris caused by the friction therebetween can be reduced. Moreover, since the engaging member 520 is the ball, when the engaging member 520 moves on the surface of the positioning member 510, it rolls and slides simultaneously, so that the debris can be further reduced.

As shown in FIGS. 2-4, the pressing assembly 600 includes a main body 610 and a pressing member 620. The main body 610 and the pressing member 620 can be assembled to form a space, and the trigger assembly 700 can be disposed in this space. In this embodiment, the pressing member 620 is a flexible film, so that when the user exerts a force on the pressing member 620, the pressing member 620 deforms and makes contact with the switch 710 of the trigger assembly 700. The storage unit 370 can therefore start to record the sound inside the human body and/or the electrical activity of the heart (electrocardiography). When the user desires to stop recording, he can provides the force on the pressing member 620, so that the pressing member 620 can be in contact with the switch 710 of the trigger assembly 700 once again.

In this embodiment, the pressing member 620 further includes a display function. For example, the pressing member 620 can include liquid-crystal display (LCD), light-emitting diode (LED), or organic light-emitting diode (OLED), and can be electrically connected to the storage unit 370 or directly electrically connected to the electrocardiogram sensor 220, the temperature sensor 230, and/or the sound recording member 360. The measured data of the electrocardiogram sensor 220, the temperature sensor 230, and/or the sound recording member 360 can transmit to the pressing member 620 and show thereon, so that it is convenient for the user to watch the aforementioned data.

The wireless transmitting unit 380 of the circuit assembly 300 is also electrically connected to the storage unit 370. Therefore, the measured data of the electrocardiogram sensor 220, the temperature sensor 230, and/or the sound recording member 360 can transmit to an external electronic device (such as a computer or a cellphone) in a wireless manner. The user can directly watch the measured data from the external electronic device.

Moreover, in this embodiment, the pressing member 620 further includes a function of touch sensing. The user can operate the inspection device E via the pressing member 620 (for example, the user can adjust the volume from the pressing member 620 when using the external headset to listen to the sound inside the human body).

Figure 10:
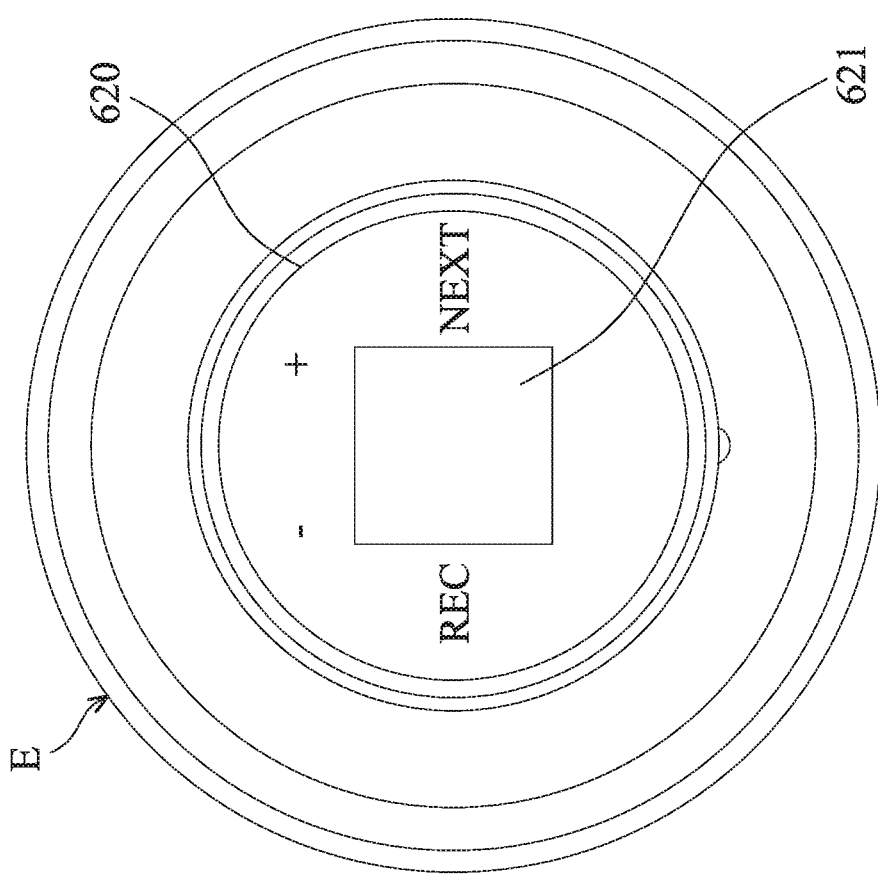
FIG. 10 is a schematic diagram of a pressing member according to some embodiments of the invention.

FIG. 10 is a schematic diagram of the pressing member 620 according to some embodiments of the invention. As shown in FIG. 10, the pressing member 620 has a liquid-crystal display 621, and the user can touch the button of the pressing member 620 to operate the inspection device E or change the display content. For example, the user can press the symbols "+" and "−" to adjust the volume of the audio outputting from the headset socket 390, press the symbol "REC" to enable the inspection device E to start recording, and press the symbol "NEXT" to change the record data shown on the liquid-crystal display 621.

In summary, an inspection device is provided, including a base, a circuit assembly, an electrocardiogram sensor, a diaphragm, an annular member, and a positioning member. The base has a top surface, a bottom surface, a guiding portion, an opening, and an accommodating space. The guiding portion is formed on the top surface, the opening is formed on the bottom surface, and the accommodating space is formed between the top surface and the bottom surface. The circuit assembly is disposed in the accommodating space, and has a first contact and a second contact. The electrocardiogram sensor is disposed on the bottom surface and electrically connected to the circuit assembly. The diaphragm covers the opening. The annular member is rotatably connected to the base and has a guiding member. The guiding member is slidably connected to the guiding portion. The positioning member is affixed to the annular member and has a contacting portion. When the annular member is in a first position relative to the base, the contacting portion is in contact with the first contact. When the annular member is in a second position relative to the base, the contacting portion is in contact with the second contact.

Although some embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, compositions of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. Moreover, the scope of the appended claims should be accorded the broadest interpretation so as to encompass all such modifications and similar arrangements.

While the invention has been described by way of example and in terms of preferred embodiment, it should be understood that the invention is not limited thereto. On the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. An inspection device, comprising:
   a base, having a bottom surface, a top surface, a guiding portion, an opening, and an accommodating space, wherein the guiding portion is formed on the top surface, the opening is formed on the bottom surface, and the accommodating space is formed between the bottom surface and the top surface;
   a circuit assembly, disposed in the accommodating space and having a first contact and a second contact;
   an electrocardiogram sensor, disposed on the bottom surface and electrically connected to the circuit assembly;
   a diaphragm, covering the opening;
   an annular member, rotatably connected to the base and having a guiding member, wherein the guiding member is slidably connected to the guiding portion; and
   a positioning member, affixed to the annular member and having a contacting portion, wherein when the annular member is in a first position relative to the base, the contacting portion is in contact with the first contact, wherein when the annular member is in a second position relative to the base, the contacting portion is in contact with the second contact.

2. The inspection device as claimed in claim 1, wherein the guiding portion is an arc-shaped slot, and the guiding member is a pillar.

3. The inspection device as claimed in claim 1, wherein the positioning member has a first recess and a second recess, and the inspection device further comprises an engaging member affixed to the base, wherein when the annular member is in the first position relative to the base, the engaging member is joined to the first recess, and when the annular member is in the second position relative to the base, the engaging member is joined to the second recess.

4. The inspection device as claimed in claim 3, wherein the positioning member is flexible.

5. The inspection device as claimed in claim 3, wherein the engaging member is a ball.

6. The inspection device as claimed in claim 1, wherein the inspection device further comprises:
   a pressing assembly, having a pressing member, wherein the pressing member is flexible; and
   a trigger assembly, having a switch, wherein when an external force is applied to the pressing member, the pressing member deforms and makes contact with the trigger assembly.

7. The inspection device as claimed in claim 6, wherein the pressing member has a display function, and is electrically connected to the circuit assembly.

8. The inspection device as claimed in claim 1, wherein the base has a through hole, and the circuit assembly comprises a headset socket, wherein the through hole communicates the accommodating space with an external environment, and a through hole of the headset socket is aligned with the through hole.

9. The inspection device as claimed in claim 1, wherein the inspection device further comprises a temperature sensor disposed on the bottom surface, and the temperature sensor is electrically connected to the circuit assembly.

10. The inspection device as claimed in claim 9, wherein the electrocardiogram sensor comprises two electrodes, and the temperature sensor is disposed between the electrodes.

\* \* \* \* \*